US011042022B2

(12) United States Patent
Yamamoto

(10) Patent No.: US 11,042,022 B2
(45) Date of Patent: Jun. 22, 2021

(54) MANUFACTURING METHOD OF OPTICAL UNIT FOR ENDOSCOPE, OPTICAL UNIT FOR ENDOSCOPE, AND ENDOSCOPE

(71) Applicant: OLYMPUS CORPORATION, Tokyo (JP)

(72) Inventor: Ken Yamamoto, Nagano (JP)

(73) Assignee: OLYMPUS CORPORATION, Tokyo (JP)

(*) Notice: Subject to any disclaimer, the term of this patent is extended or adjusted under 35 U.S.C. 154(b) by 227 days.

(21) Appl. No.: 16/214,228

(22) Filed: Dec. 10, 2018

(65) Prior Publication Data
US 2019/0113738 A1 Apr. 18, 2019

Related U.S. Application Data

(63) Continuation of application No. PCT/JP2016/067766, filed on Jun. 15, 2016.

(51) Int. Cl.
*G02B 7/02* (2021.01)
*B29D 11/00* (2006.01)
(Continued)

(52) U.S. Cl.
CPC .......... *G02B 23/243* (2013.01); *A61B 1/0011* (2013.01); *A61B 1/00096* (2013.01); *B29D 11/0074* (2013.01); *B29D 11/00307* (2013.01); *B29D 11/00403* (2013.01); *G02B 3/0037* (2013.01); *G02B 7/02* (2013.01);
(Continued)

(58) Field of Classification Search
CPC .............................. B29D 11/00307
See application file for complete search history.

(56) References Cited

U.S. PATENT DOCUMENTS

2008/0180566 A1  7/2008 Singh
2010/0053318 A1  3/2010 Sasaki
(Continued)

FOREIGN PATENT DOCUMENTS

JP  2010056292 A  3/2010
JP  2010098066 A  4/2010
(Continued)

OTHER PUBLICATIONS

International Search Report dated Sep. 6, 2016 issued in PCT/JP2016/067766.

*Primary Examiner* — Marc C Howell
*Assistant Examiner* — John J DeRusso
(74) *Attorney, Agent, or Firm* — Scully, Scott, Murphy & Presser, P.C.

(57) ABSTRACT

A manufacturing method of an optical unit for endoscope includes: a process of crimping a bonding sheet including a curable resin film to a release substrate having a release surface which is an optical flat surface; a mirror-finishing process of performing a partial curing treatment on a predetermined region of the bonding sheet to process the predetermined region into an optical flat surface; a process of fabricating a laminated wafer by laminating a first element wafer including a first optical element and a second element wafer including a second optical element, with the bonding sheet being arranged between the first element wafer and the second element wafer; a curing process of performing a curing treatment on an uncured region of the bonding sheet; and a process of cutting the laminated wafer and segmenting the laminated wafer into optical units.

5 Claims, 14 Drawing Sheets

(51) Int. Cl.
  *G02B 23/24*  (2006.01)
  *G02B 23/26*  (2006.01)
  *A61B 1/00*  (2006.01)
  *G02B 3/00*  (2006.01)
  *A61B 1/05*  (2006.01)
  *H01L 27/146*  (2006.01)
  *H04N 5/225*  (2006.01)

(52) U.S. Cl.
  CPC ......... *G02B 23/2423* (2013.01); *G02B 23/26* (2013.01); *A61B 1/051* (2013.01); *H01L 27/14618* (2013.01); *H01L 27/14625* (2013.01); *H04N 5/2254* (2013.01); *H04N 2005/2255* (2013.01)

(56) References Cited

U.S. PATENT DOCUMENTS

| | | | |
|---|---|---|---|
| 2010/0091168 A1 | 4/2010 | Igarashi et al. |
| 2013/0265481 A1 | 10/2013 | Singh |
| 2015/0026971 A1 | 1/2015 | Singh |

FOREIGN PATENT DOCUMENTS

| | | | |
|---|---|---|---|
| JP | 2010517432 A | 5/2010 |
| JP | 2011118166 A | 6/2011 |
| JP | 2011197186 A | 10/2011 |
| JP | 2012018993 A | 1/2012 |
| JP | 2013205587 A | 10/2013 |
| JP | 2014239446 A | 12/2014 |
| JP | 2015064435 A | 4/2015 |
| WO | 2008094499 A2 | 8/2008 | ced
MANUFACTURING METHOD OF OPTICAL UNIT FOR ENDOSCOPE, OPTICAL UNIT FOR ENDOSCOPE, AND ENDOSCOPE

CROSS REFERENCE TO RELATED APPLICATION

This application is a continuation application of PCT/JP2016/067766 filed on Jun. 15, 2016, the entire contents of which are incorporated herein by this reference.

BACKGROUND OF INVENTION

1. Field of the Invention

The present invention relates to a manufacturing method of an optical unit for endoscope configured by laminating a plurality of optical elements, an optical unit for endoscope configured by laminating a plurality of optical elements, and an endoscope including an optical unit for endoscope configured by laminating a plurality of optical elements.

2. Description of the Related Art

In an optical unit for endoscope to be disposed in an endoscope, size reduction, in particular, reduction in the diameter size is significant for achieving low invasion.

Japanese Patent Application Laid-Open Publication No. 2012-18993 discloses a manufacturing method of an optical unit constituted of a wafer-level laminated body, as a method of efficiently manufacturing an optical unit. The wafer-level optical unit is fabricated by cutting and segmenting a laminated wafer formed by laminating a plurality of element wafers each including a plurality of optical elements and by bonding the plurality of element wafers with adhesive.

Japanese Patent Application Laid-Open Publication No. 2011-197186 and Japanese Patent Application Laid-Open Publication No. 2014-239446 propose a bonding method of lens wafers (element wafers) using a solid adhesive sheet (bonding sheet) as adhesive for bonding the element wafers.

Commonly, the bonding sheet is sandwiched by two release films. The release film on one surface of the bonding sheet is peeled off, and the one surface from which the film is peeled off is pasted on a first wafer, and thereafter a release film on the other surface of the bonding sheet is peeled off. Then, the first wafer on which the bonding sheet is pasted is crimped to a second wafer, to thereby bond the two wafers.

SUMMARY OF THE INVENTION

A manufacturing method of an optical unit for endoscope according to an embodiment of the present invention is a manufacturing method of an optical unit for endoscope which includes: a first optical element including a first optical path portion and a first spacer portion surrounding the first optical path portion; a second optical element including a second optical path portion and a second spacer portion surrounding the second optical path portion; and a sheet-like bonding portion including a curable resin film and bonding the first optical element and the second optical element, the sheet-like bonding portion including a center portion which is in contact with an optical path space, and a peripheral portion that bonds the first spacer portion and the second spacer portion and surrounds the center portion, and the manufacturing method includes: a process of fabricating a first element wafer including the first optical element and a second element wafer including the second optical element; a process of preparing a bonding sheet including the curable resin film; a partial curing process of performing curing treatment on a predetermined region of the bonding sheet; a mirror-finishing process of processing a surface of the predetermined region into an optical flat surface; a process of fabricating a laminated wafer by laminating the first element wafer and the second element wafer, with the bonding sheet being disposed between the first element wafer and the second element wafer such that the predetermined region of the bonding sheet is opposed to the first optical path portion and the second optical path portion; a curing process of performing curing treatment on an uncured region of the bonding sheet in the laminated wafer; and a process of cutting the laminated wafer.

An optical unit for endoscope according to an embodiment of the present invention includes: a first optical element including a first optical path portion and a first spacer portion surrounding the first optical path portion; a second optical element including a second optical path portion and a second spacer portion surrounding the second optical path portion; and a sheet-like bonding portion including a curable resin film that bonds the first optical element and the second optical element, and the sheet-like bonding portion includes a center portion which is in contact with an optical path space and forms an optical path, and a peripheral portion bonding the first spacer portion and the second spacer portion and surrounding the center portion, and a surface of the center portion, which is in contact with the optical path space, is an optical flat surface.

An endoscope according to an embodiment of the present invention includes an optical unit for endoscope, and the optical unit for endoscope includes: a first optical element including a first optical path portion and a first spacer portion surrounding the first optical path portion; a second optical element including a second optical path portion and a second spacer portion surrounding the second optical path portion; and a sheet-like bonding portion including a curable resin film that bonds the first optical element and the second optical element, and the sheet-like bonding portion includes a center portion which is in contact with an optical path space and forms an optical path, and a peripheral portion bonding the first spacer portion and the second spacer portion and surrounding the center portion, and a surface of the center portion, which is in contact with the optical path space, is an optical flat surface.

DETAILED DESCRIPTION OF THE PREFERRED EMBODIMENT(S)

First Embodiment

Figure 1:
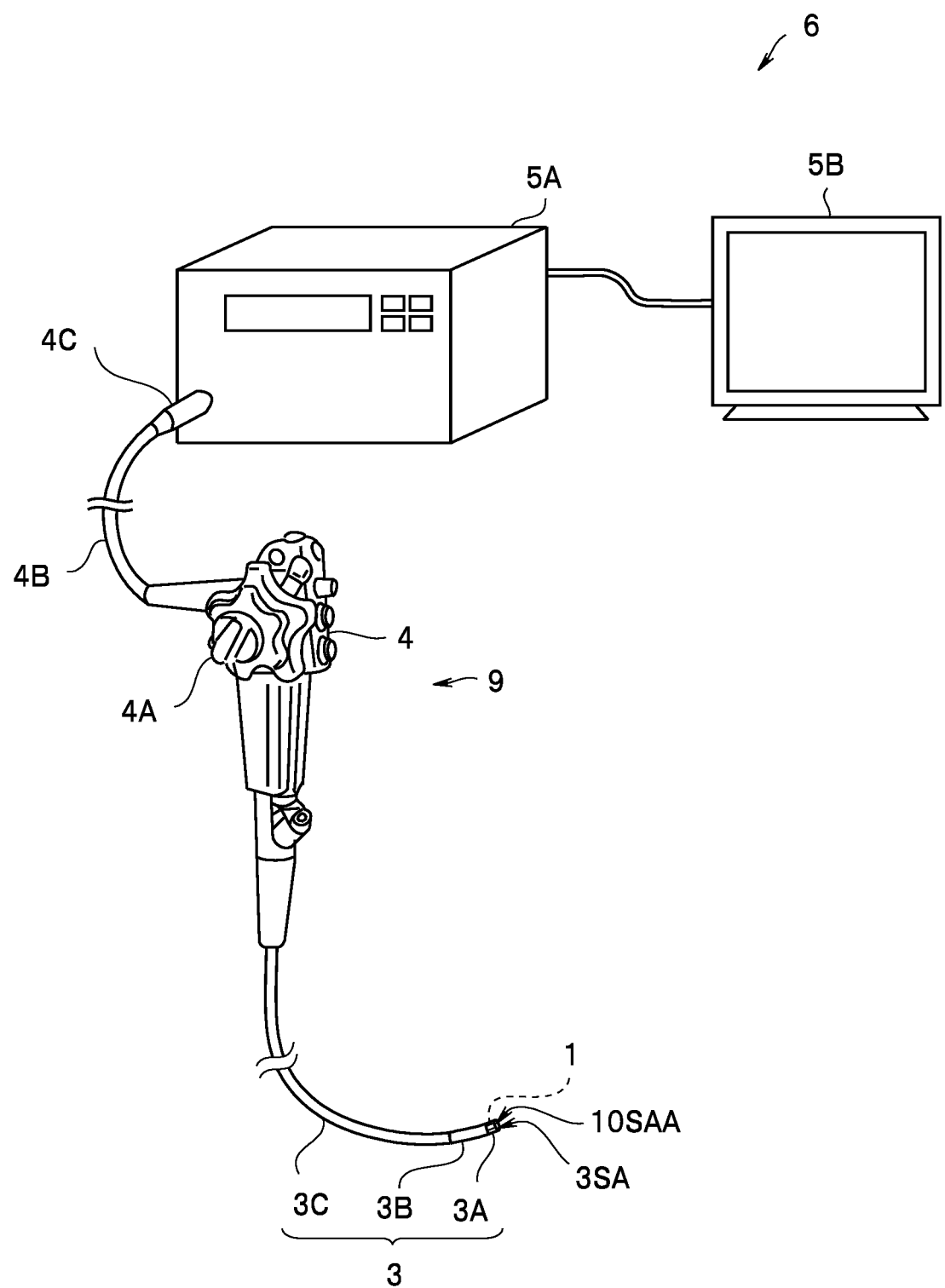
FIG. 1 is a perspective view of an endoscope according to an embodiment.

As shown in FIG. 1, an optical unit for endoscope 1 (hereinafter, also referred to as "optical unit 1") according to the present embodiment is disposed at a distal end portion 3A of an insertion portion 3 of an endoscope 9.

Note that each of the drawings based on each of the embodiments is a pattern diagram in the description below, and care should be taken to the fact that the relationship between the thicknesses and widths of the respective parts, a ratio of the thicknesses, relative angles, and the like of the respective parts are different from the actual ones, and there is a case where the respective drawings include the parts in which the relationships and ratios among the dimensions are different from those in other drawings. In addition, there is a case where illustration of some constituent elements is omitted.

An endoscope 9 includes the insertion portion 3, a grasping portion 4 disposed on a proximal end portion side of the insertion portion 3, a universal cord 4B extended from the grasping portion 4, and a connector 4C disposed on a proximal end portion side of the universal cord 4B. The insertion portion 3 includes a distal end portion 3A at which the optical unit 1 is disposed, a bending portion 3B extended from the proximal end side of the distal end portion 3A and configured to be bendable and change a direction of the distal end portion 3A, and a flexible portion 3C extended from the proximal end side of the bending portion 3R The optical unit 1 includes a light incident surface 10SAA exposed on a distal end surface 3SA of the distal end portion 3A. The grasping portion 4 is provided with an angle knob 4A configured to rotate. The angle knob 4A is an operation portion configured to be operated by an operator to operate the bending portion 3B.

The universal cord 4B is connected to the processor 5A through a connector 4C. The processor 5A is configured to control an entire endoscope system 6, perform signal processing on an image pickup signal outputted from the optical unit 1, and output the image pickup signal subjected to the signal processing as an image signal. A monitor 5B displays the image signal outputted from the processor 5A as an endoscopic image. Note that the endoscope 9 is a flexible endoscope. However, the endoscope 9 may be a rigid endoscope as long as the endoscope includes a bending portion. That is, the flexible portion and the like are not essential constituent elements of the endoscope according to the embodiment. In addition, the endoscope according to the embodiment may be a capsule endoscope including the optical unit 1.

<Configuration of Optical Unit>

Figure 2:
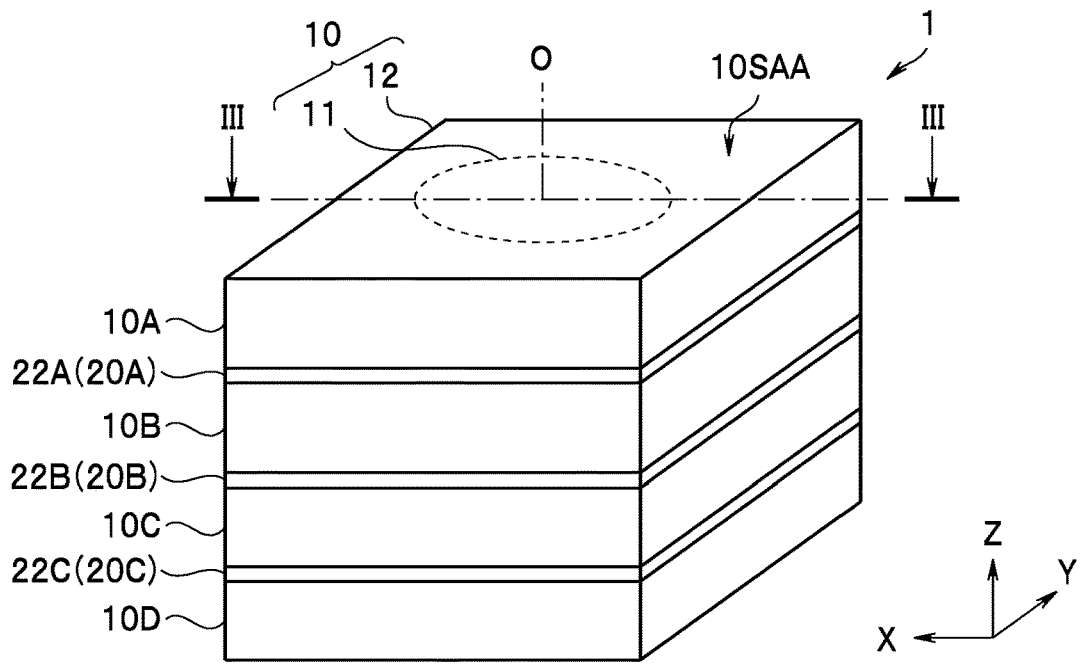
FIG. 2 is a perspective view of an optical unit according to a first embodiment.
Figure 3:
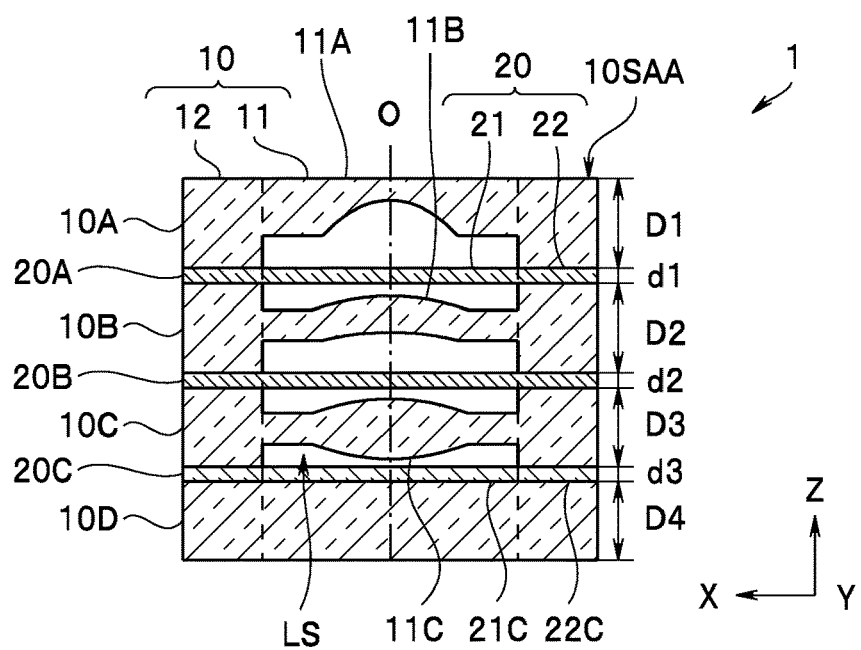
FIG. 3 is a cross-sectional view taken along the line in FIG. 2 of the optical unit according to the first embodiment.
Figure 4:
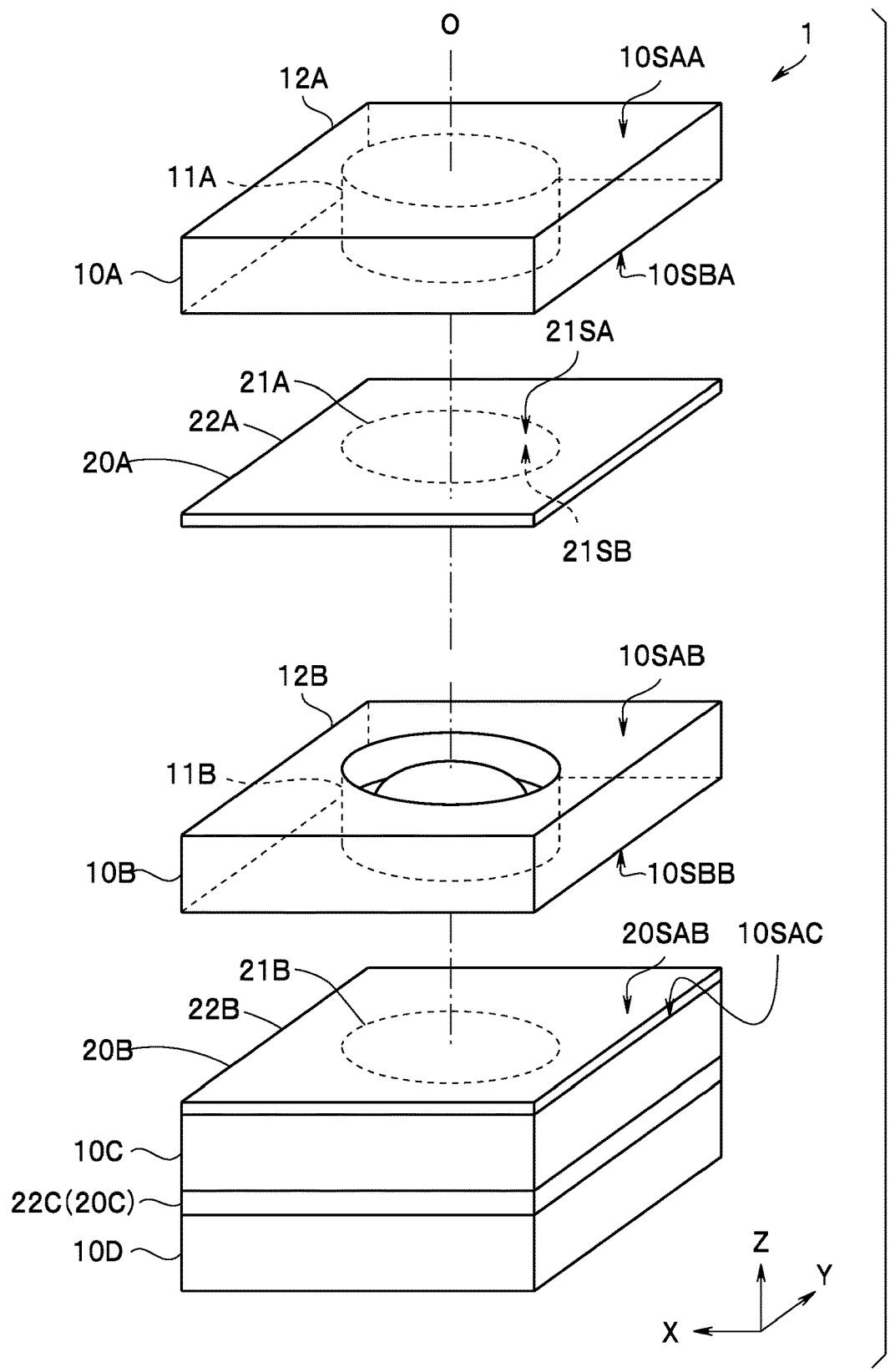
FIG. 4 is an exploded view of the optical unit according to the first embodiment.

As shown in FIGS. 2 to 4, the optical unit for endoscope 1 is a laminated body formed by laminating a first optical element 10A, a second optical element 10B, a third optical element 10C, and a fourth optical element 10D.

Note that, hereinafter, when referring to each of a plurality of constituent elements, one alphabetic character at the end of the respective reference signs will be omitted. For example, each of the first optical element 10A to the fourth optical element 10D will be referred to as the optical element 10.

The plurality of optical elements 10 are bonded to one another by sheet-like bonding portions (hereinafter, also referred to as "bonding portions") 20 disposed between the respective optical elements. That is, a rear surface 10SBA of the first optical element 10A and a front surface 10SAB of the second optical element 10B are bonded to each other through a first sheet-like bonding portion 20A made of a curable resin film. A rear surface 10SBB of the second optical element 10B and a front surface 10SAC of the third optical element 10C are bonded to each other through a second sheet-like bonding portion 20B. The third optical element 10C and the fourth optical element 10D are bonded to each other through a third sheet-like bonding portion 20C.

Figure 11:
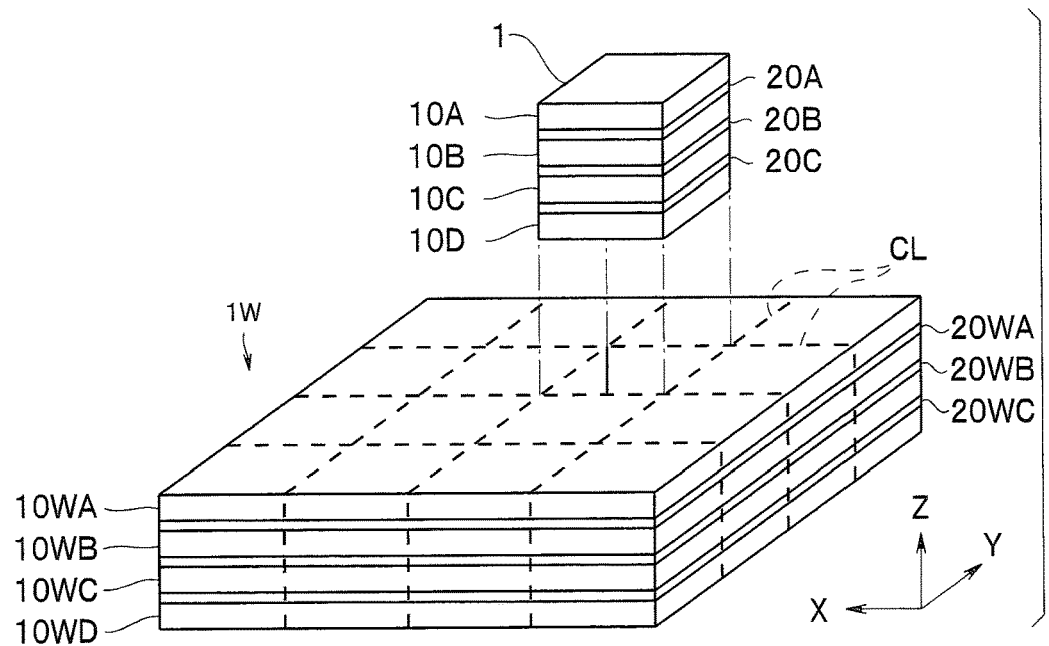
FIG. 11 is a perspective view of a cutting process of the laminated wafer according to the first embodiment.

The optical unit 1 is a wafer-level optical unit fabricated by cutting a laminated wafer 1W (see FIG. 11). Therefore, both of the optical element 10 and the bonding portion 20 have a square shape and the same outer dimension in the cross section taken along the direction orthogonal to the optical axis. In addition, the plurality of optical elements 10 are laminated such that the optical axes O of the optical elements coincide with each other.

The optical element 10 includes an optical path portion 11 that configures an optical path and a spacer portion 12 surrounding the optical path portion 11 with no gap. For example, an optical path portion 11 A of the optical element 10A has a circular shape in a plan view, and has a front surface 10SAA which is a flat plate incident surface and a rear surface 10SBA which is a concave lens. That is, the optical path portion 11A is, what is called, a plano-concave lens. The spacer portion 12A has a square outer shape and a circular inner shape in a plan view, and includes a bonding surf ace protruded in the optical axis direction with respect to the optical path portion 11A.

An optical path portion 11B of the optical element 10B is a concave-shaped negative meniscus lens having a convex-shaped front surface 10SAB and a concave-shaped rear surface 10SBB. An optical path portion 11C of the optical element 10C is a convex lens both surfaces of which are convex-shaped. The optical element 10D is an infrared cut filter made of a parallel flat plate.

The bonding portion 20 that bonds the optical elements 10 opposed to each other is roughly divided into a circular center portion 21 disposed on the optical path and a ringshaped peripheral portion 22 surrounding the center portion 21 with no gap. That is, a bonding portion 20A includes a center portion 21A and a peripheral portion 22A, a bonding portion 20B includes a center portion 21B and a peripheral portion 22B, and a bonding portion 20C includes a center portion 21C and a peripheral portion 22C.

However, the boundary between the center portion 21 and the peripheral portion 22 is not clear enough to distinguish between the center portion 21 and the peripheral portion 22. As described later, in the manufacturing process, the center portion 21 and the peripheral portion 22 are the regions adjacent to each other on one bonding sheet 20W (see FIG. 10) and made of the same curable resin.

Note that the thicknesses D1 to D4 of the optical elements 10A to 10D and the thicknesses d1 to d3 of the bonding portions 20A to 20C are set according to specifications.

In the optical unit 1, for example, the part between the optical path portion 11B of the optical element 10B and the center portion 21A of the bonding portion 20A is an optical path space LS where no solid optical member exists. As already described above, in an optical unit using a conventional bonding sheet, the surface property of the bonding sheet (bonding portion) which is in contact with the optical path space LS is not excellent.

In contrast, the optical unit 1 is manufactured by the manufacturing method to be described later. Therefore, though the front surface 21SA and the rear surface 21SB of the center portion 21A of the bonding portion 20A are in contact with the optical path space LS, for example, these surfaces are optical flat surfaces. Here, the optical flat surface means a plane with surface irregularity equal to or less than one-fourth of the shortest wavelength λ of wavelengths of the light whose image is picked up by the endoscope 9, and can be optically regarded as a plane, but the surface accuracy of the plane is not enough to serve as a lens. Furthermore, the front surface 21SA and the rear surface 21SB of the center portion 21A of the bonding portion 20A are formed to be parallel to each other, that is, the bonding portion 20A is, what is called, optical parallel.

When the optical unit 1 configures a visible light optical system, a plane having a surface accuracy, with the surface irregularity being 100 nm (λ/4) with respect to the light of λ=400 nm which is the shortest wavelength of the visible light, is an optical flat surface. The surface accuracy is measured by the interferometric technique using a reference substrate having surface accuracy of λ/10 or more, for example.

Note that the optical unit 1 also includes other optical elements such as a flare diaphragm and a brightness diaphragm, though not shown. In addition, any of the optical elements may be a spacer element, including, at the center thereof, a through hole which serves as an optical path. That is, the configuration of the optical unit according to the embodiment is not limited to the configuration of the optical unit 1. The configuration such as the numbers of the optical elements, spacers, and the diaphragms are set according to the specifications of the optical unit.

The essential constituent elements of the optical unit according to the present embodiment are the first optical element 10A, the second optical element 10B, and the first sheet-like bonding portion 20A.

That is, the optical unit for endoscope 1 includes: at least one first optical element 10A including the first optical path portion 11A and the first spacer portion 12A; at least one second optical element 10B including the second optical path portion 11B and the second spacer portion 12B; and the sheet-like bonding portion 20A that bonds the first optical element 10A and the second optical element 10B. The sheet-like bonding portion 20A includes the center portion 21A which is in contact with the optical path space LS and forms the optical path, and the peripheral portion 22A that bonds the first spacer portion 12A and the second spacer portion 12B, and the surfaces 21SA, 21SB of the center portion 21A, which are in contact with the optical path space LS, are optical flat surfaces.

The optical unit 1 is formed by bonding the element wafers 10W with the bonding sheet 20W, which prevents a bad influence on the optical property of the optical unit due to the protrusion of the adhesive to the optical path space. In addition, there is no need for forming an opening in the optical path region of the bonding sheet 20W, which enables easy manufacturing. Furthermore, in the optical unit 1, the surfaces 21SA, 21SB of the center portion 21 which forms the optical path are optical flat surfaces on which light is not scattered, thereby providing an excellent optical property.

The endoscope 9 including the optical unit 1 has a thin diameter, and is easy to manufacture and has high reliability.

<Manufacturing Method of Optical Unit for Endoscope>

Figure 5:
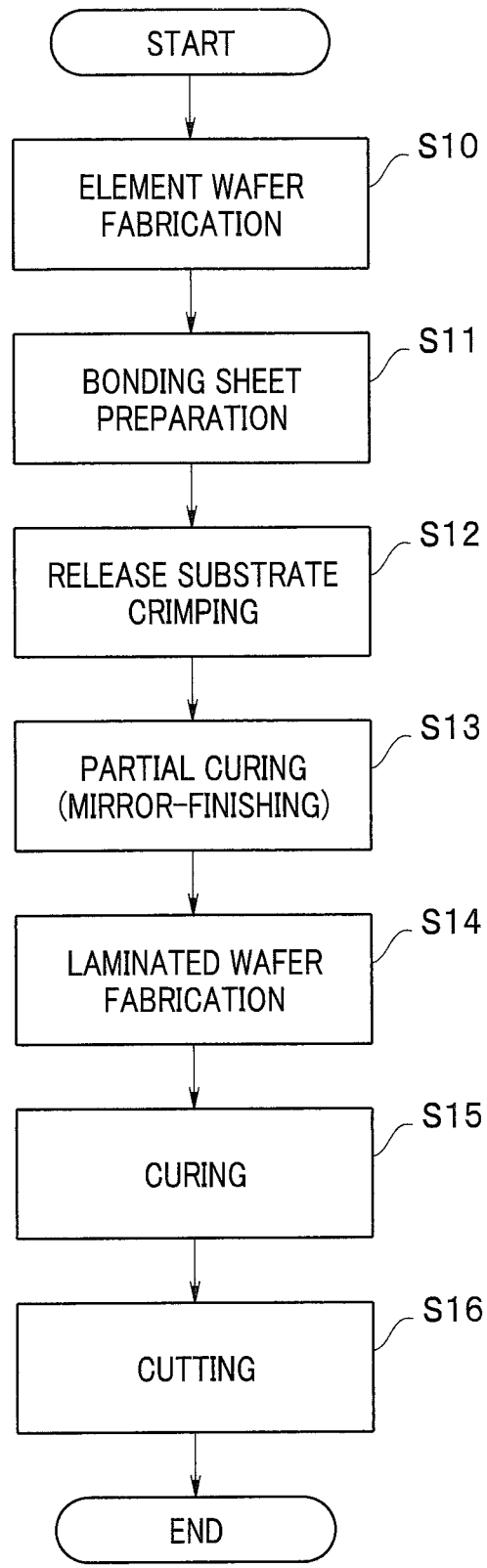
FIG. 5 is a flowchart of a manufacturing method of the optical unit according to the first embodiment.

Next, the manufacturing method of the optical unit for endoscope according to the present embodiment will be described referring to the flowchart in FIG. 5. The optical unit 1 is a wafer-level optical unit manufactured by cutting and segmenting the laminated wafer 1W (see FIG. 11) including a plurality of optical units.

<Step S10> Element Wafer Fabrication Process

Figure 6:
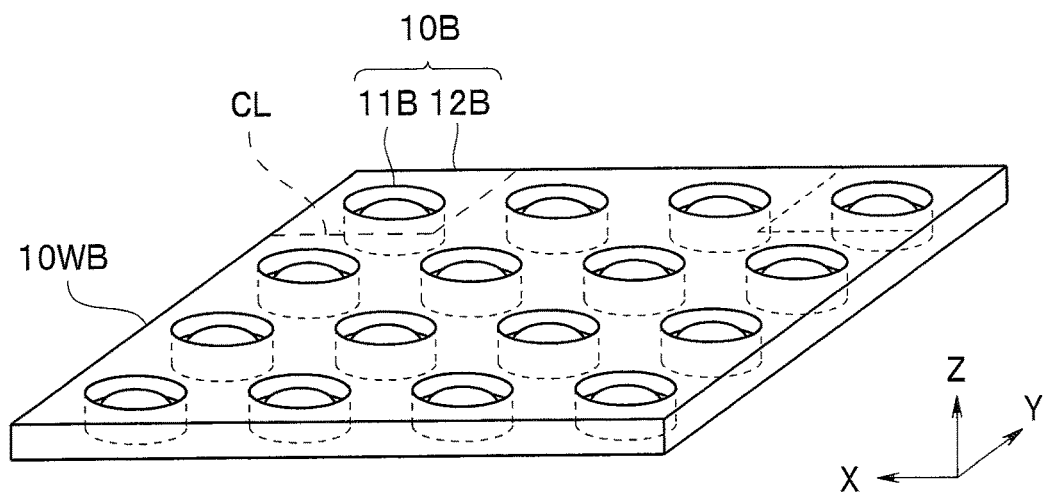
FIG. 6 is a perspective view of an element wafer according to the first embodiment.

A plurality of element wafers 10WA to 10WD are fabricated based on the specifications. For example, as shown in FIG. 6, the element wafer 10WB is a square wafer on which sixteen optical elements 10B, each of which includes the optical path portion 11B and the spacer portion 12B surrounding the optical path portion 11B, are arranged in a matrix form. The boundary lines between the respective adjacent element wafers 10W are cutting lines CL (see FIG. 11) to be used in the cutting process to be described later. That is, in the state of the element wafer 10W, the spacer portion 12 is a parallel flat plate region that surrounds the optical path portion 11.

The element wafers 10WA to 10WC are made of transparent optical resin such as polycarbonate. The element wafer 10WB including a plurality of optical path portions 11B having a predetermined shape is fabricated by molding the optical resin using a metal mold by an injection molding method or by a press molding method, for example. The shape of the metal mold is transferred to the shape of the element wafer 10W, which enables aspherical lenses to be easily fabricated as the optical path portions 11.

Note that the parallel flat plate element wafer 10WD is a parallel flat plate filter wafer made of an infrared cut material that removes the infrared rays. As the filter wafer, a plate glass wafer including, on the surface thereof, a band-pass filter that transmits only the light of a predetermined wavelength and cuts the light of unnecessary wavelength may be used.

The element wafer 10W has only to be transparent in the wavelength band of the light in the specifications of the optical unit, and may be fabricated by performing etching treatment on a glass such as a borosilicate glass, a quartz glass, or a single-crystal sapphire, for example. Alternatively, the element wafer 10W may be a hybrid lens wafer formed by disposing, on a parallel flat plate wafer, the optical path portion 11 and the spacer portion 12 that are made of resin.

As already described above, the configuration of the element wafer 10W, that is, the material of the element wafer, the shape, number, arrangement, and outer shape of the optical elements 10 disposed on the element wafer are designed according to the specifications of the optical unit. However, it is preferable that the numbers and the arrangements of the optical elements 10A to 10C on the element wafers 10WA to 10WC are the same.

<Step S11> Bonding Sheet Preparation Process

Figure 7:
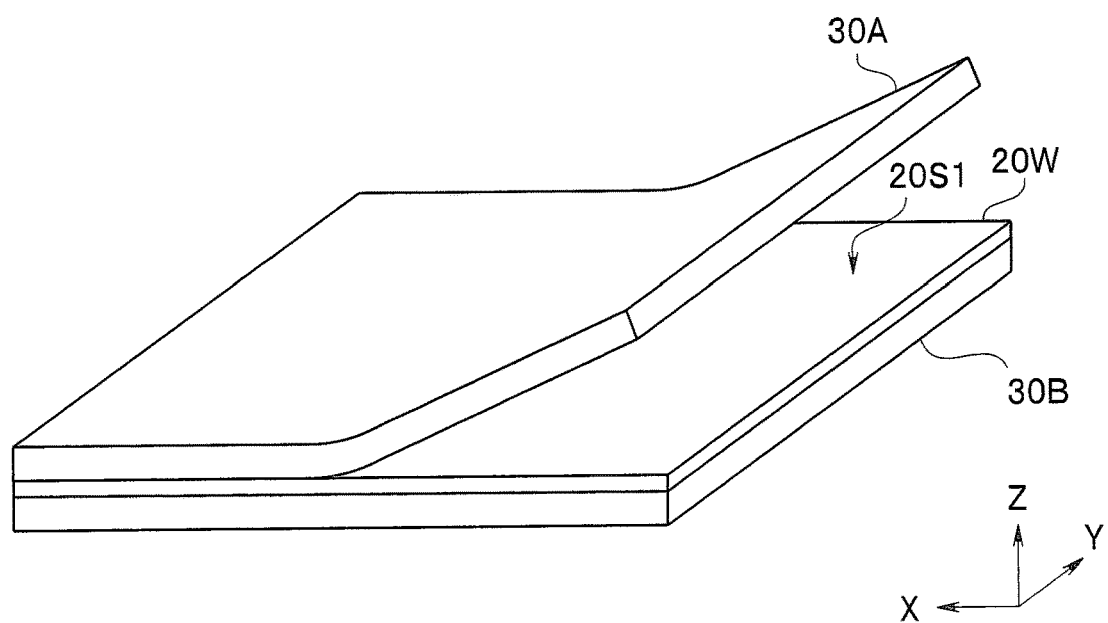
FIG. 7 is a perspective view of a bonding sheet according to the first embodiment.

The bonding sheet 20W is prepared. As shown in FIG. 7, the bonding sheet 20W is sandwiched by two release films 30A, 30B, for example. The bonding sheet 20W which is an adhesive film made of uncured and adhesive curable resin is fabricated by applying resin to the release film 30. In addition, a commercially available adhesive sheet in desired specifications may be used as the bonding sheet 20W. Note that the order of the element wafer fabrication process and the bonding sheet preparation process may be reversed.

The bonding sheet 20W according to the present embodiment is made of acrylic ultraviolet curable resin. The bonding sheet 20W has a thickness of 25 μm, a light transmissivity of (400 nm) 99.8%, and a refractive index of 1.49.

As the curable resin of the bonding sheet 20W, natural rubber, acrylic resin, ethylene-vinyl acetate copolymer, polyurethane, polyester, silicone rubber, fluororubber, polyvinylbutyral, or the like is used. The curable resin may include tackifier, adhesive modifiers, anti-aging agents, stabilizer, coloring agent, and the like.

When the curable resin is an ultraviolet curable resin, the curable resin includes a curing agent such as polyisocyanate compound and a polymerization initiator such as benzoin derivative. When the curable resin is a heat curable resin, the curable resin includes a polymerization initiator such as azo compound, peroxide, or the like.

In addition, the release surface of the release film 30 having a base body made of PET or the like is processed with a release agent such as silicone, wax, fluororesin, or the like so as to be releasable. When the material of the release film 30 is fluroresin which shows releasing property, release treatment is not necessary.

The surface 25S1 of the adhesive bonding sheet 20W from which the release film 30 is peeled off has irregularity, and is not an optical flat surface. Therefore, when the element wafers 10WA and 10WB are bonded to each other with the bonding sheet 20WA, the surface of the center portion 21A, which is in contact with the optical path space LS of the optical unit, has irregularity, and the light is scattered on the surface.

Figure 8:
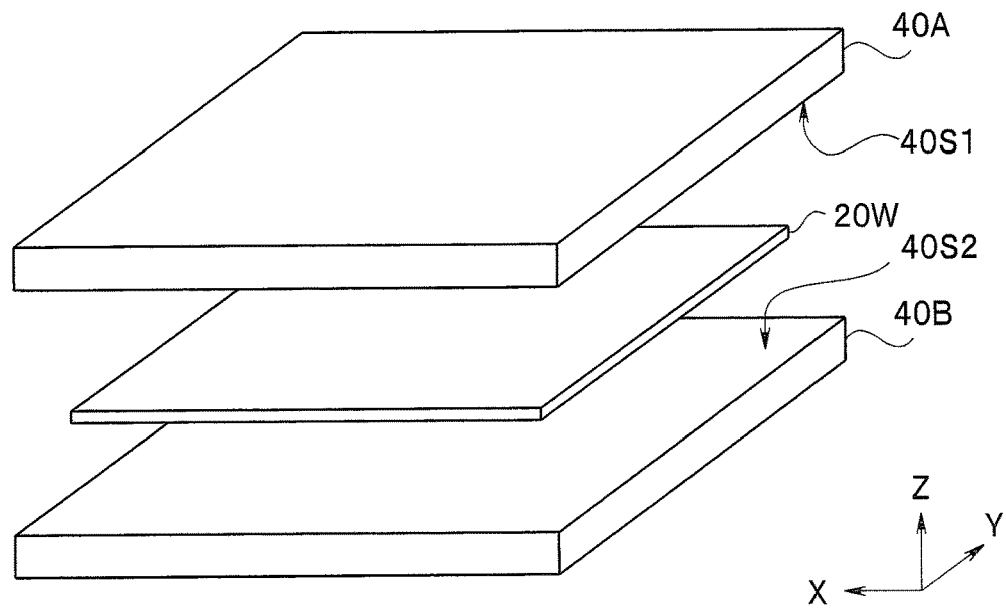
FIG. 8 is a perspective exploded view of the bonding sheet sandwiched by support substrates according to the first embodiment.
Figure 9:
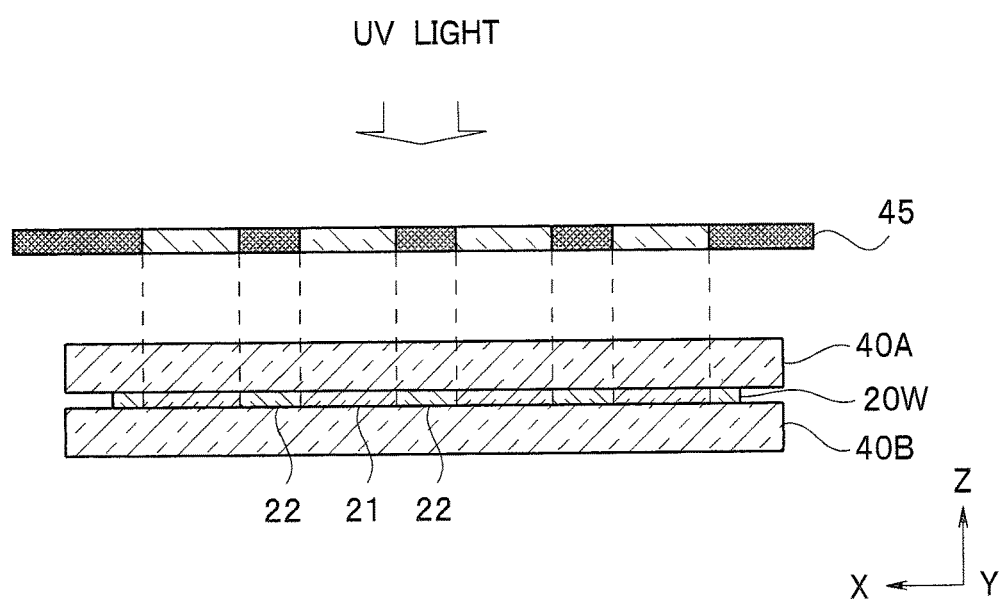
FIG. 9 is a cross-sectional view of a partial curing process of the bonding sheet according to the first embodiment.

Therefore, as shown in FIGS. 8 and 9, in the manufacturing method according to the present embodiment, mirror-finishing process is performed for processing the surface of the predetermined region (center portion 21) of the bonding sheet 20W into the optical flat surface. In the manufacturing method according to the present embodiment, the mirror-finishing process is performed simultaneously with a partial curing treatment of the bonding sheet 20W.

<Step S12> Release Substrate Crimping Process

As shown in FIG. 8, the bonding sheet 20W is sandwiched and crimped by two release substrates 40A, 40B. The release substrates 40A, 40B are held in parallel so as to be separated from each other by a distance which is a little smaller than the thickness of the bonding sheet 20W. The release substrates 40A, 40B are rigid substrates, for example, glass substrates, with the release surfaces 40S1, 40S2 that sandwich the bonding sheet 20W being optical flat surfaces.

The release substrates 40A, 40B are fabricated as follows. The surfaces of the glass substrates are processed into the optical flat surfaces according to the predetermined specifications by polishing processing, and thereafter release treatment is performed on the surfaces. Note that, when the bonding sheet 20W is the ultraviolet curable resin, one of the release substrates, i.e., the release substrate 40A is a transparent substrate that transmits the ultraviolet rays.

The front surface and the rear surface of the bonding sheet 20W crimped by the two release substrates 40A, 40B that are in parallel have the same shapes as those of the surfaces of the release surfaces 40S1, 40S2, and are optical flat surfaces. That is, the bonding sheet 20W is, what is called, optical parallel.

Note that when the release films 30A, 30B sandwiching the bonding sheet 20W are made of a material that transmits the ultraviolet rays and the release surfaces are optical flat surfaces, the release film 30 may be used as the release substrate.

However, if the release films 30A, 30B sandwiching the bonding sheet 20W are flexible, it is preferable to perform partial exposure process, with the bonding sheet 20W being sandwiched by non-flexible substrates, for example, in order to improve the patterning accuracy.

Note that the upper surface of the third bonding sheet 20WC is in contact with the optical path space, but no space exists in the optical path on the lower surface of the third bonding sheet 20WC. Therefore, the third bonding sheet 20WC may be crimped by the release substrate 40A and the element wafer 10WD.

<Step S13> Partial Curing Process (Mirror-Finishing Process: First Curing Process)

As shown in FIG. 9, a plurality of predetermined regions of the bonding sheet 20W crimped by the two release substrates 40A, 40B are subjected to the curing treatment. Each of the predetermined regions is a circular region which is the center portion 21 of the optical unit 1.

The plurality of predetermined regions (center portions) 21 of the bonding sheet 20W cure by being irradiated with the ultraviolet light through a photo mask 45, and lose adhesiveness. The peripheries (peripheral portions) 22 of the predetermined regions, which are not irradiated with the ultraviolet light, are remained uncured and has adhesiveness.

The surfaces 21SA, 21SB of each of the predetermined regions (center portions) 21 are subjected to the curing treatment (crimping molding) in the state being crimped by the release substrates 40. Since the surfaces 21SA, 21SB are replica surfaces on which the shapes of the crimping surfaces of the release substrates are transferred and have been cured, the surfaces are the optical flat surfaces even if the release substrates 40 are peeled off.

That is, in the manufacturing method according to the present embodiment, the partial curing treatment process is also the mirror-finishing process for processing the surfaces of the predetermined regions into the optical flat surfaces.

When the curable resin is a thermosetting resin, the partial curing process is performed by partially heating only the predetermined region by spot irradiation of laser light, for example.

<Step S14> Laminated Wafer Fabrication Process

Figure 10:
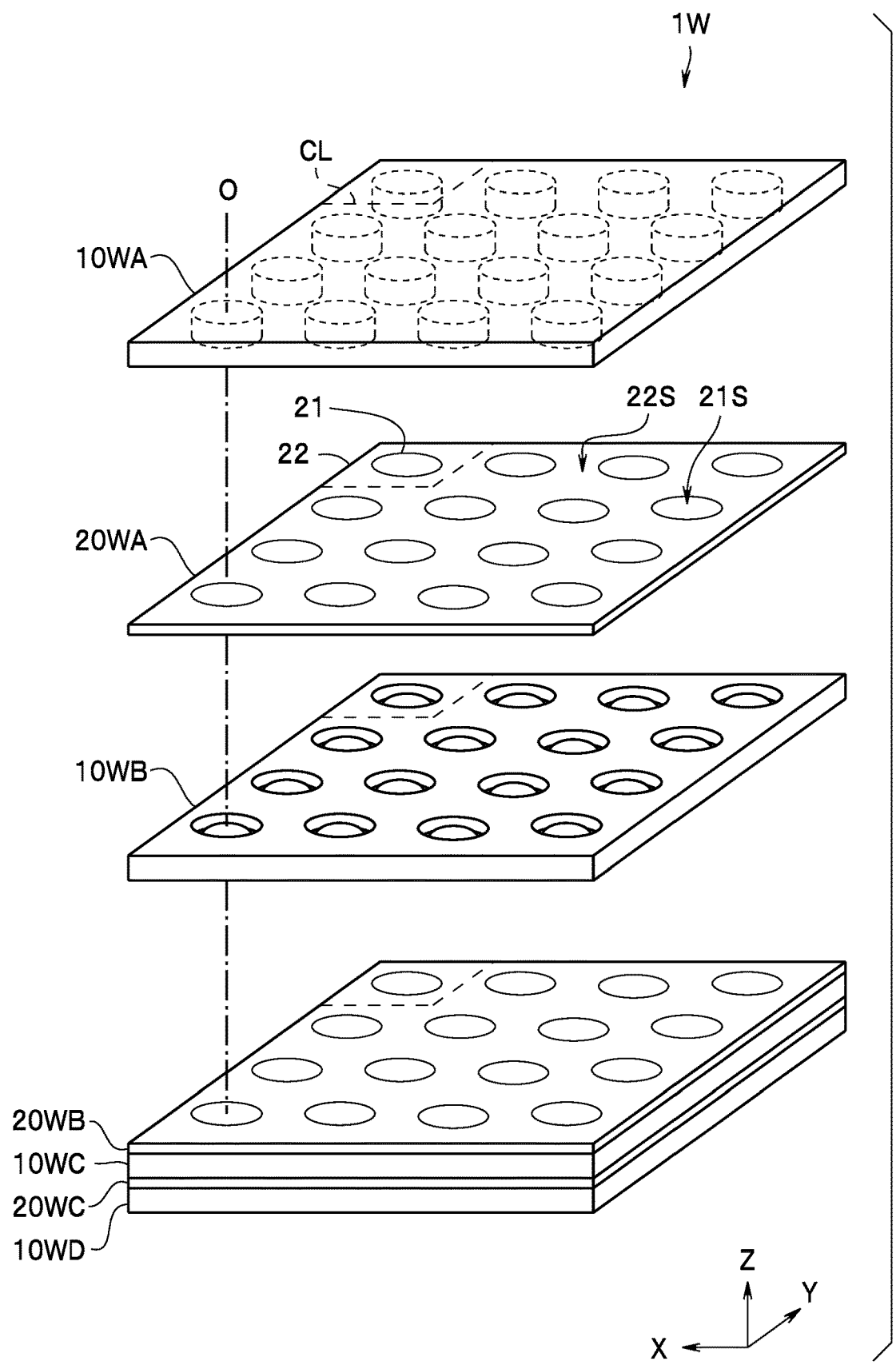
FIG. 10 is an exploded view of a laminated wafer according to the first embodiment.

As shown in FIG. 10, the element wafers 10WA to 10WD and the bonding sheets 20WA to 20WC are positioned such that the optical axes O of the optical elements 10A to 10D coincide with the center of the center portion 21, to be crimped and laminated, to thereby fabricate the laminated wafer 1W.

That is, the release substrate 40A is peeled off from the bonding sheet 20W sandwiched by the release substrates 40A, 40B, and the bonding sheet 20W is bonded to the element wafer 10W. Then, the release substrate 40B is peeled off, and the bonding sheet 20W is bonded to another element wafer 10W.

As already described above, since the regions (peripheral portions 22) of the bonding sheet 20W other than the predetermined regions are uncured and have adhesiveness, the surfaces 22S from which the release substrate 40 is peeled off have irregularity. On the other hand, since the surfaces 21S of the predetermined regions (center portions 21) of the bonding sheet 20W are cured, the surfaces 21S are the replica surfaces on which the shape of the crimping surface of the release substrate 40 is transferred. That is, the surfaces 21S are optical flat surfaces even if the release substrate 40 is peeled off.

Note that the laminated wafer fabrication process is preferably performed in a depressurized state below an atmospheric pressure, for example, in a depressurized state equal to or lower than 0.1 atmospheric pressure. The pressure in the sealed optical path space LS is lower than the atmospheric pressure, which prevents the breakage of the laminated wafer due to an expansion of gas in the optical path space LS caused by heating in a subsequent process, for example, a reflow process. Note that the lower limit of the pressure is preferably set to 0.001 atmospheric pressure or higher, for example, for simplification of the manufacturing processes.

<Step S15> Curing Process (Second Curing Process)

When the bonding sheet 20W is the ultraviolet curable resin, the laminated wafer 1W is irradiated with the ultraviolet rays, and when the bonding sheet 20W is the thermosetting resin, heating treatment is performed, and thereby the element wafers 10W opposed to each other through the peripheral portion 22 of the bonding sheet 20W are firmly bonded to each other.

<Step S16> Cutting Process

As shown in FIG. 11, the laminated wafer 1W including the plurality of optical units 1 is cut and segmented along the cutting lines CL by a dicing blade. The cutting may be performed by laser dicing or plasma dicing.

The manufacturing method according to the present embodiment prevents the adhesive from protruding to the optical path space and eliminates the need for forming an opening on the bonding sheet 20W, which enables easy manufacturing. Furthermore, in the manufactured optical unit 1, the surface 21S of the center portion 21, which is in contact with the optical path space, is the optical flat surface on which light is not scattered. Such a configuration provides the excellent optical property.

Modified Example of First Embodiment

Next, description will be made on an optical unit for endoscope 1A according to the modified example of the first embodiment. The optical unit 1A is similar to the optical unit 1 and has the same effects as those of the optical unit 1. The same constituent elements are attached with the same reference numerals and descriptions thereof will be omitted.

Figure 12:
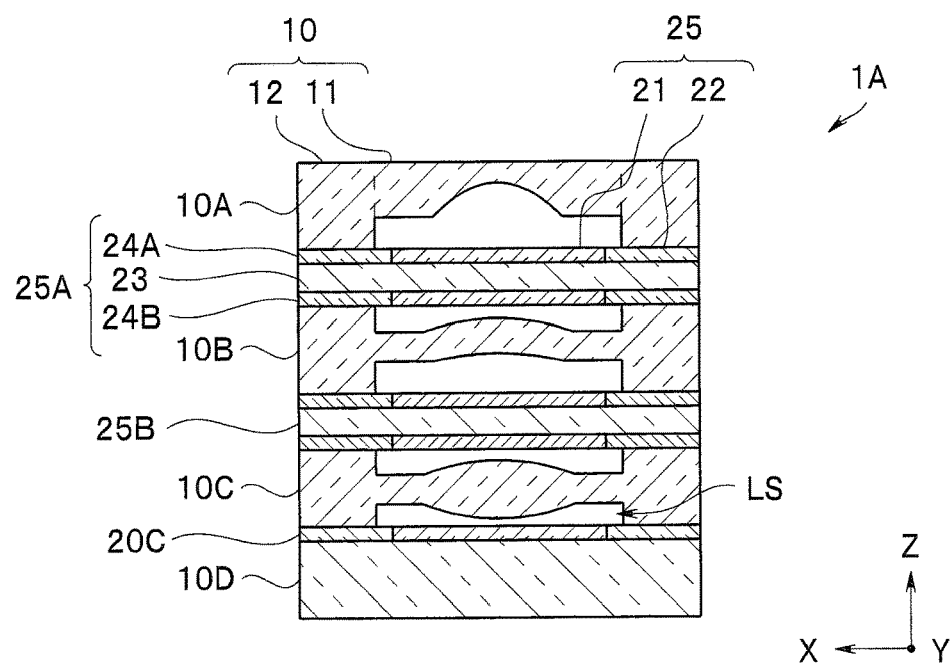
FIG. 12 is a cross-sectional view of an optical unit according to a modified example 1 of the first embodiment.

As shown in FIG. 12, in the optical unit 1A, a sheet-like bonding portion 25 (25A, 25B) is a double-sided bonding portion formed by disposing curable resin films 24A, 24B respectively on both surfaces of a transparent parallel flat plate element 23. That is, the bonding sheet that bonds the element wafers is the double-sided sheet formed by disposing the curable resin films respectively on the both surfaces of the transparent parallel flat plate sheet, though not shown.

In the optical unit 1, the both surfaces of the center portion 21 of the sheet-like bonding portions 20A, 20B are in contact with the optical path space. Such a configuration cannot completely eliminate the possibility that the sheet-like bonding portion deforms when laminating the wafers, to cause degradation of the optical property of the optical unit 1. In contrast, the sheet-like bonding portion 25 of the optical unit 1A has the parallel flat plate element 23 as the base body. Therefore, the curable resin films 24A, 24B, which are disposed on the parallel flat plate element 23, are not likely to be deformed, which prevents the degradation of the optical property of the optical unit 1A. Furthermore, the sheet-like bonding portion 25 is capable of using the parallel flat plate element 23 as a spacer for defining the spacing between the optical elements 10 to a desired spacing.

Note that a sheet-like bonding portion 20C of the optical unit 1A is configured such that only one surface is in contact with the optical path space LS. Therefore, the sheet-like bonding portion 20C that bonds the optical element 10C and the optical element 10D is not a double-sided bonding portion. It is needless to say that the double-sided bonding sheet may be used for bonding the element wafer 1 OWC and the element wafer 10WD.

As described above, the optical unit for endoscope according to the embodiment includes the first optical element, the second optical element, and the sheet-like bonding portion. The first optical element includes the first optical path portion and the first spacer portion surrounding the first optical path portion with no gap. The second optical element includes the second optical path portion and the second spacer portion surrounding the second optical path portion with no gap. The sheet-like bonding portion includes at least one curable resin film and bonds the first spacer portion of the first optical element and the second spacer portion of the second optical element. The sheet-like bonding portion includes the center portion which is in contact with the optical path space and the peripheral portion that bonds the first spacer portion and the second spacer portion and surrounds the center portion.

The manufacturing method of the optical unit for endoscope according to the embodiment includes: a process of fabricating the first element wafer including the plurality of first optical elements and the second element wafer including the plurality of second optical elements; a process of preparing the bonding sheet including at least one sheet-like bonding portion; a partial curing process of performing curing treatment on a plurality of predetermined regions of the bonding sheet; a mirror-finishing process of processing the surfaces of the plurality of predetermined regions into optical flat surfaces; a process of fabricating the laminated wafer by laminating the first element wafer and the second element wafer, with the bonding sheet being disposed between the first element wafer and the second element wafer such that the plurality of respective predetermined regions of the bonding sheet are opposed to the first optical path portions of the plurality of first optical elements and the second optical path portions of the plurality of second optical elements; a curing process of performing curing treatment on the uncured regions around the plurality of predetermined regions of the bonding sheet in the laminated wafer; and a process of cutting the laminated wafer and segmenting the laminated wafer into the plurality of optical units.

Second Embodiment

Next, description will be made on an optical unit for endoscope 1B according to the second embodiment. The optical unit 1B is similar to the optical unit 1. The same constituent elements are attached with the same reference numerals and descriptions thereof will be omitted.

Figure 13:
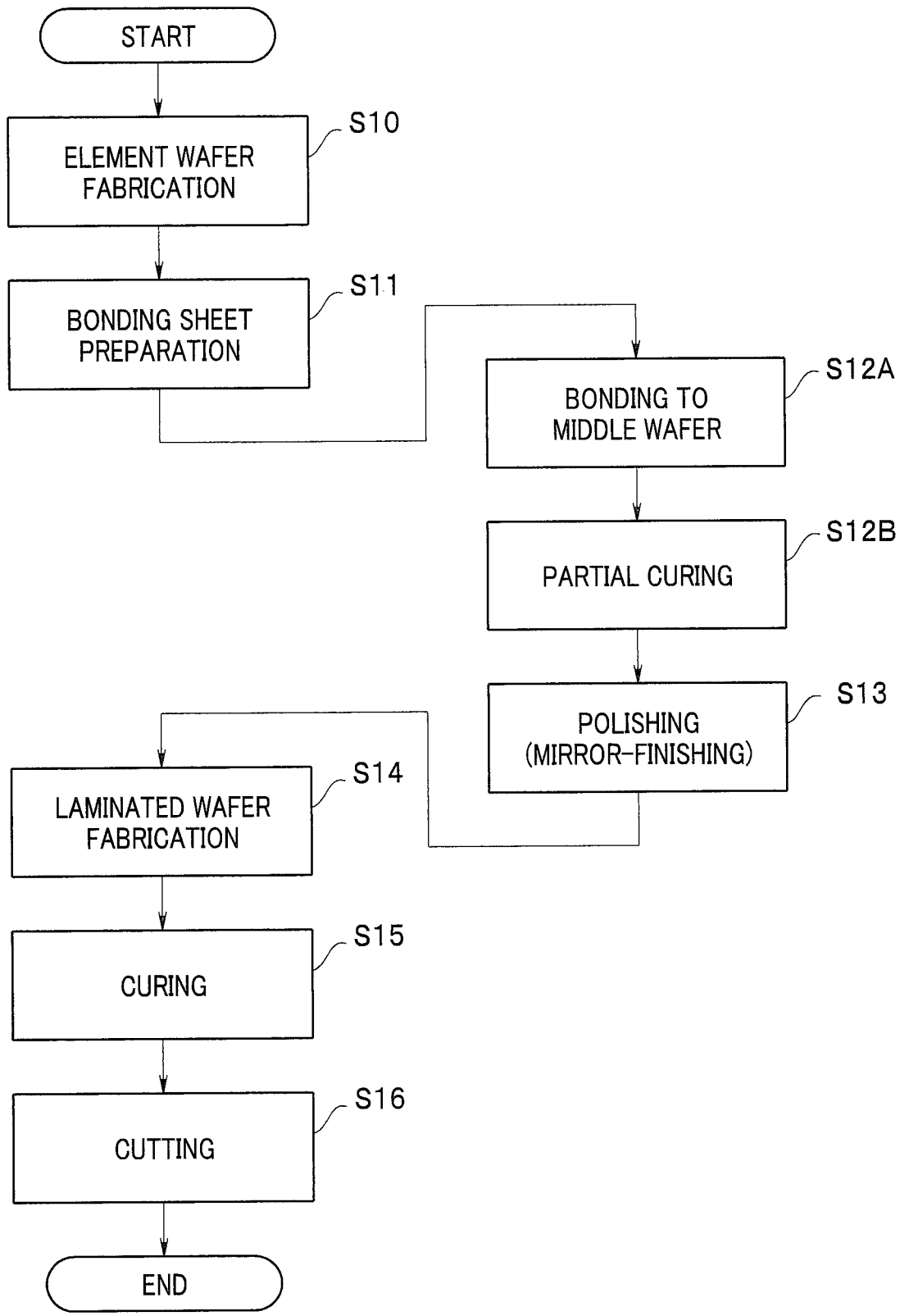
FIG. 13 is a flowchart of a manufacturing method of an optical unit according to a second embodiment.

As shown in the flowchart in FIG. 13, in the manufacturing method of the optical unit 1B, the mirror-finishing process (S13) is a machining process of mechanically processing the surfaces of the predetermined regions, which have been subjected to the curing treatment, of the bonding sheet 20W.

Steps S10, S11 are the same as those in the manufacturing method of the optical unit 1 according to the first embodiment as described above.

<Step S12A> Middle Wafer Bonding Process

The bonding sheet 20W from which the release film 30 is peeled off is bonded to a release surface 15SA of a middle wafer 15. The middle wafer 15 may be a non-transparent substrate such as a silicon wafer, but the release surface 15SA is an optical flat surface subjected to the release treatment. Note that, if a release film 30B is sufficiently thick and the release surface of the release film is an optical flat surface, the release film 30B on one side of the bonding sheet 20W may be used as the middle wafer 15.

<Step S12B> Partial Curing Process

Figure 14:
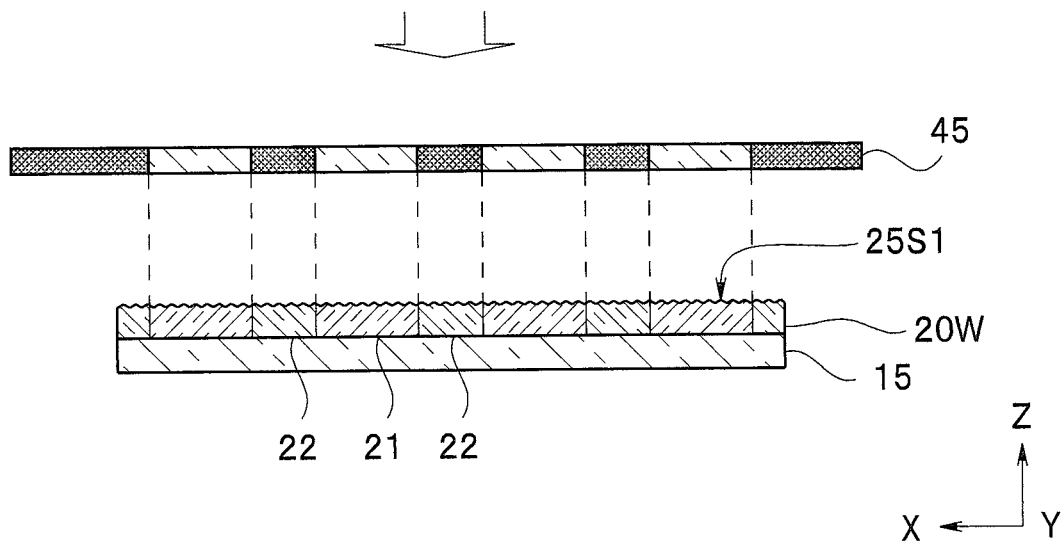
FIG. 14 is a cross-sectional view of a partial curing process of a bonding sheet according to the second embodiment.

As shown in FIG. 14, the surface 25S1 of the bonding sheet 20W from which a release film 30A is peeled off has irregularity. A plurality of predetermined regions of the bonding sheet 20W bonded to the middle wafer 15 are subjected to the curing treatment. Each of the predetermined regions is a circular region which serves as the center portion 21 of the optical unit 1B.

<Step S13> Polishing Process (Mirror-Finishing Process)

Figure 15:
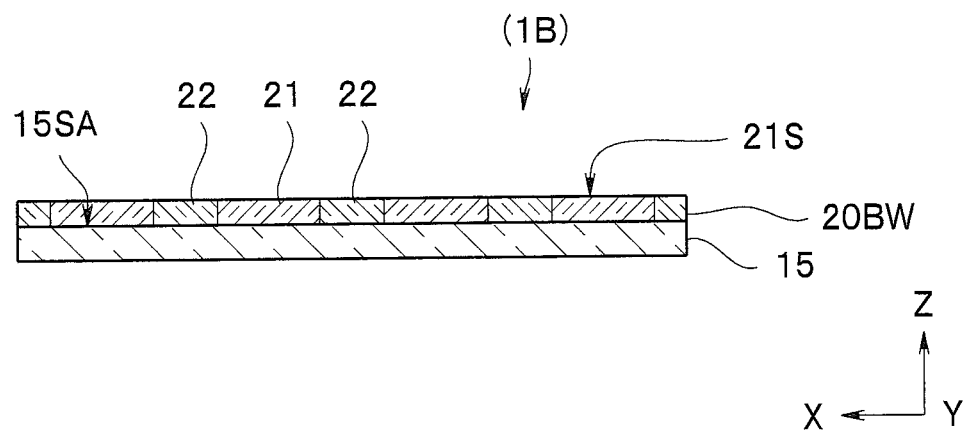
FIG. 15 is a cross-sectional view of the bonding sheet according to the second embodiment.

The surfaces of the partially cured predetermined regions (center portions 21) of the bonding sheet 20W have irregularity. The bonding sheet 20BW shown in FIG. 15 is the bonding sheet 20W whose surface is processed into the optical flat surface. The mirror-finishing process is a grinding/polishing machining process and may be a CMP process including a chemical processing.

Note that the surface of a bonding sheet 20BW, which is peeled off from the optical flat surface of the middle wafer 15, is an optical flat surface. In addition, the front surface and the rear surface of the bonding sheet 20BW are flat and parallel to each other, that is, the bonding sheet 20BW is, what is called, "optical parallel".

The steps S14 to S16 are the same as the steps in the manufacturing method of the optical unit 1 according to the first embodiment already described above, except that the bonding sheet 20BW is used as the bonding sheet.

Note that, if the surface of the middle wafer 15 is not an optical flat surface, a transparent substrate which is not subjected to release treatment is used as the middle wafer 15, the bonding sheets 20W are bonded respectively to the both surfaces of the substrate, and a double-sided sheet is fabricated by the partial curing process/polishing process.

In the optical unit 1B, the element wafers 10W are bonded using the bonding sheet 20BW, and the surface 21S of the center portion 21, which is in contact with the optical path space, is the optical flat surface, which enables easy manufacturing and provides an excellent optical property of the optical unit.

Third Embodiment

Next, description will be made on an optical unit for endoscope 1C according to the third embodiment of the present invention. The optical unit 1C is similar to the optical unit 1B. The same constituent elements are attached with the same reference numerals and descriptions thereof will be omitted.

Figure 16:
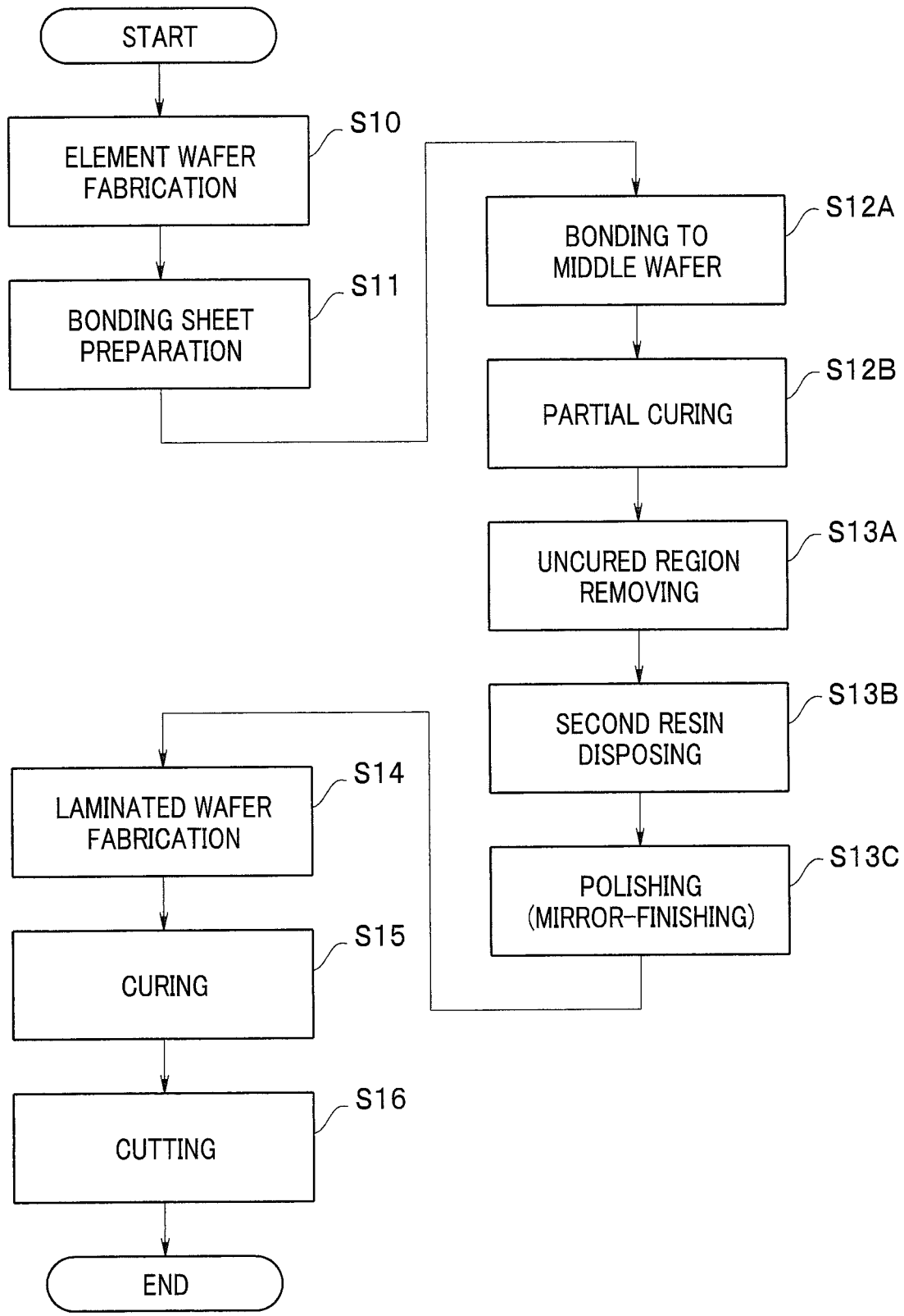
FIG. 16 is a flowchart of a manufacturing method of an optical unit according to a third embodiment.

As shown in the flowchart in FIG. 16, the manufacturing method of the optical unit 1C further includes a process S13A of removing a curable resin film on the uncured regions, a process S13B of disposing a second curable resin film, and a polishing process (mirror-finishing process) S13C, after the partial curing process S12B.

The steps S10, S11, S12A, and S12B are the same as those in the manufacturing method of the optical unit 1B.

<Step S13A> Uncured Region Removing Process

Figure 17:
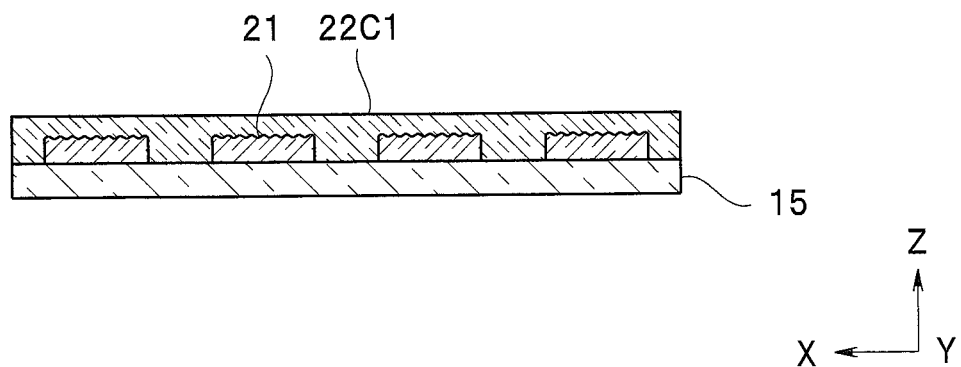
FIG. 17 is a cross-sectional view of a bonding sheet according to the third embodiment.

As shown in FIG. 17, the uncured regions (peripheral portions) of the bonding sheet are removed. For example, the uncured film around the predetermined regions (center portions 21) is removed with an organic solvent such as acetone by using the difference between the solubility of the cured film on the predetermined regions (center portions 21) in the solvent and the solubility of the uncured film in the solvent.

<Step S13B> Second Resin Disposing Process

Furthermore, similarly as the first curable resin film, an adhesive second curable resin film 22C1 is disposed on the entire surface including the regions from which the uncured film is removed.

<Step S13C> Polishing Process (Mirror-Finishing Process)

Figure 18:
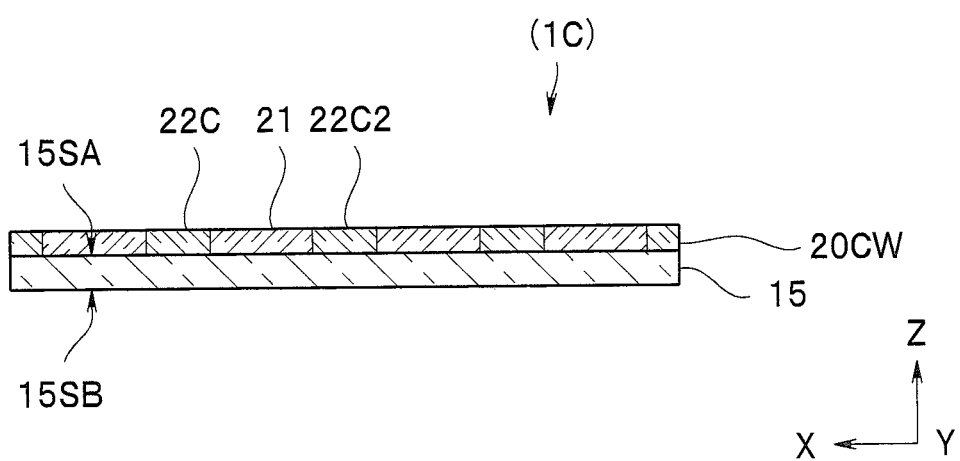
FIG. 18 is a cross-sectional view of the bonding sheet according to the third embodiment.

As shown in FIG. 18, in the polishing process S13C, the predetermined regions (center portions 21) are mechanically processed into optical flat surfaces, and into, what is called, "optical parallel". That is, the second curable resin film 22C1 on the predetermined regions (center portions 21) is mechanically removed, and the surfaces of the cured predetermined regions (center portions 21), which are located under the removed second curable film, become the optical flat surfaces.

The center portions 21 made of the cured first curable resin and the peripheral portions 22C2 made of the uncured adhesive second curable resin are integrated to constitute one bonding sheet 20CW.

Note that, before the mirror-finishing process S13C, the second curable resin film on the predetermined regions (center portions 21) may be removed by photolithography/etching, or the like. Alternatively, the second curable resin film may be disposed only around the predetermined regions (center portions 21) by the ink-jet method, the printing method, or the like. However, the thickness of the second curable resin film 21C is equal to or thicker than the thickness of each of the predetermined regions (center portions 21).

The steps S14 to S16 are the same as the steps in the manufacturing methods of the optical unit 1 and the optical unit 1B according to the first embodiment already described above, except that the bonding sheet 20CW is used as the bonding sheet.

In the optical unit 1C, the element wafers 10W are bonded using the bonding sheet 20CW, and the surface of the center portion 21, which is in contact with the optical path space, is the optical flat surface, which enables easy manufacturing and provides an excellent optical property of the optical unit.

Note that, similarly as the optical unit 1B, if the surface of the middle wafer 15 is not an optical flat surface, a double-sided sheet is fabricated by using a transparent middle wafer which is not subjected to the release treatment.

In addition, the material of the second curable resin film may be the same as or different from the material of the first curable resin film. Furthermore, the center portion may be made of glass, or the like, instead of the resin.

Modified Examples of Third Embodiment

An optical unit for endoscope 1D and an optical unit for endoscope 1E according to the modified examples of the third embodiment are similar to the optical units 1 to 1C, and have the same effects as those of the optical units 1 to 1C. The same constituent elements are attached with the same reference numerals and descriptions thereof will be omitted.

Modified Example 1 of Third Embodiment

Figure 19:
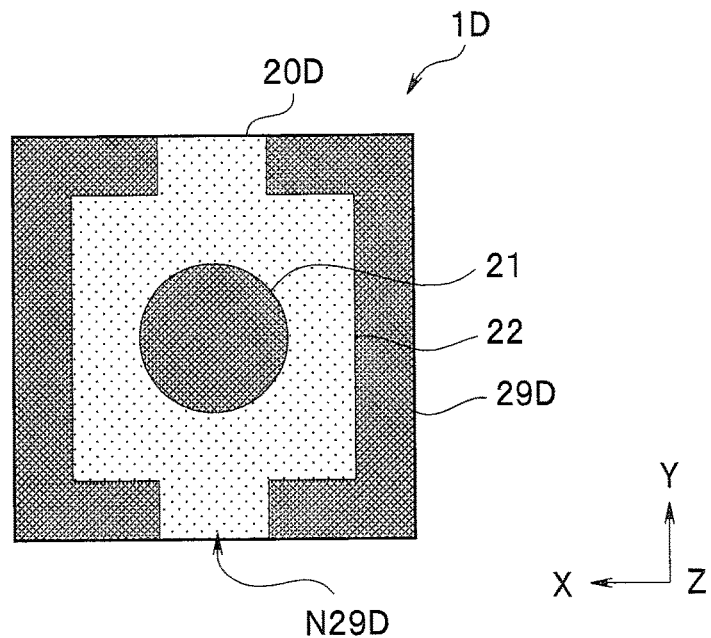
FIG. 19 is a top view of a bonding portion according to a modified example 1 of the third embodiment.

As shown in FIG. 19, in the optical unit for endoscope 1D according to the modified example 1 of the third embodiment, the bonding portion 20D is configured such that not only the center portion 21 which is an optical path but also a surrounding region 29D of the peripheral portion 22 is subjected to the curing treatment simultaneously with the center portion 21.

Note that cutouts N29D are formed in the surrounding region 29D. The cutouts N29D are not essential configuration of the surrounding region 29D. However, when the plurality of element wafers 10W are crimped to fabricate the laminated wafer, if the uncured resin (peripheral portion) expands by heat, which may cause deformation of the center portion 21. Therefore, it is preferable to form the cutouts N29D for pushing the excessive uncured resin to the outside of the cutouts.

Modified Example 2 of Third Embodiment

Figure 20:
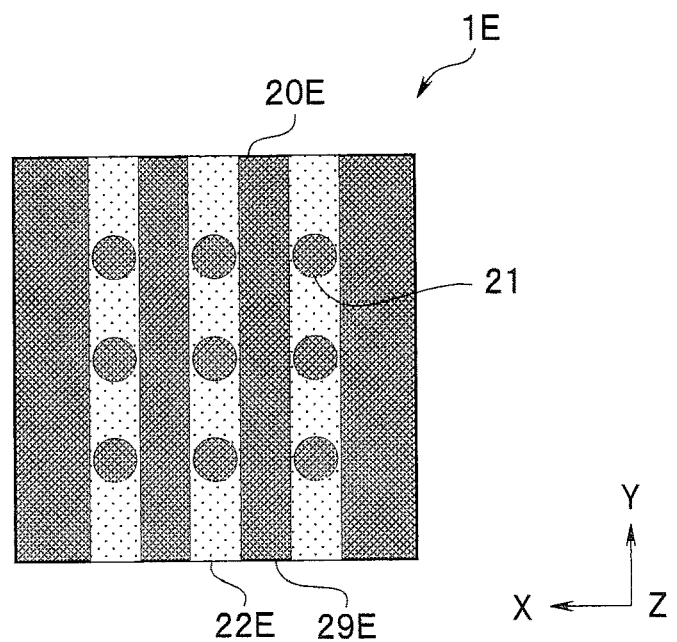
FIG. 20 is a top view of a bonding portion according to a modified example 2 of the third embodiment.

As shown in FIG. 20, the optical unit for endoscope 1E according to the modified example 2 of the third embodiment is an array optical unit including a plurality of optical paths.

A bonding portion 20E of the optical unit 1E includes a plurality of center portions 21 corresponding to the plurality of optical paths, and peripheral portions 22E are formed in a stripe shape so as to enclose the plurality of center portions 21. Periphery regions 29E of the peripheral portions 22 subjected to the partial curing treatment simultaneously with the center portions 21 are also formed in a stripe shape. That is, the shape of the peripheral portions 22 is not limited to a circular shape, or the like.

Fourth Embodiment

An optical unit for endoscope 1F according to the fourth embodiment is similar to the optical units for endoscope 1 to 1E, and has the same effects as those of the optical units 1 to 1E. The same constituent elements are attached with the same reference numerals and descriptions thereof will be omitted.

Figure 21:
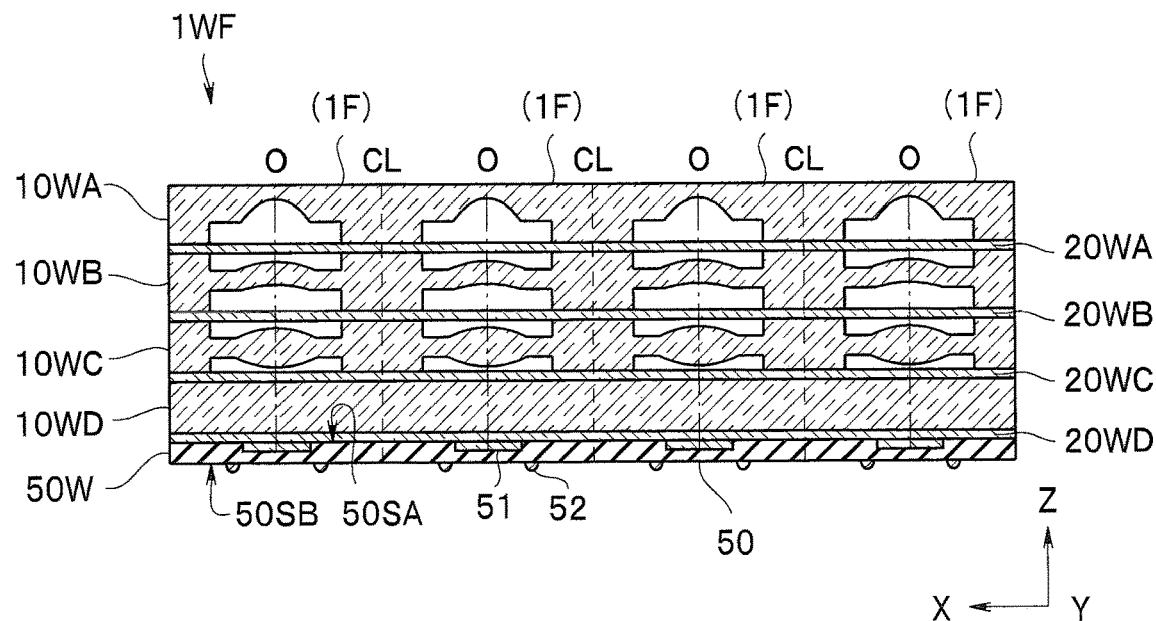
FIG. 21 is a cross-sectional view of a laminated wafer according to a fourth embodiment.

As shown in FIG. 21, in the laminated wafer fabrication process S14 of the optical unit 1F according to the fourth embodiment, a laminated wafer 1WF is fabricated, in which an image pickup device wafer 50W including a plurality of image pickup devices 50 is bonded as an element wafer through a bonding sheet 20WD.

The image pickup device wafer 50W made of a silicon wafer includes a plurality of image pickup devices 50 each including, on a light-receiving surface 50SA, a light-receiving portion 51 formed by a known semiconductor manufacturing technique. An electrode 52 connected to the light-receiving portion 51 through the through-wiring (not shown) is disposed on the rear surface 50SB of each of the image pickup devices 50. The image pickup device wafer 50W may include a reading circuit.

Figure 22:
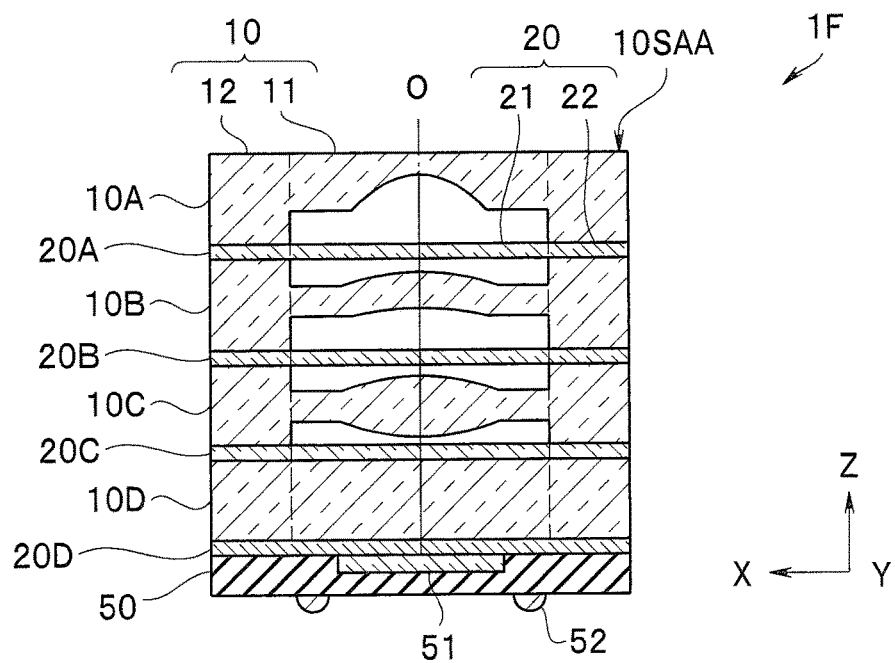
FIG. 22 is a cross-sectional view of an optical unit according to the fourth embodiment.

As shown in FIG. 22, the optical unit 1F fabricated by cutting the laminated wafer 1WF is an image pickup unit further including the image pickup device 50 in the configuration of the optical unit 1.

The light received at the light-receiving portion 51 of the image pickup device 50 through the optical elements 10A to 10D is converted into an electric signal and outputted from the electrode 52.

Note that, it is needless to say that each of the optical units 1B to 1F has the effects of the optical unit 1A and the like according to the modified example of the first embodiment, if each of the optical units 1B to 1F includes the configuration of the optical unit 1A and the like, for example. Furthermore, it is needless to say that the endoscope including each of the optical units 1A to 1F has the effects of the endoscope 9 including the optical unit 1, and further includes the effects of each of the optical units 1A to 1F.

The present invention is not limited to the above-described embodiments and the like, and various changes, modifications, and the like are possible without changing the gist of the present invention.

What is claimed is:

1. A manufacturing method of an optical unit for endoscope,
the optical unit for endoscope comprising:
   a first optical element including a first optical path portion and a first spacer portion surrounding the first optical path portion;
   a second optical element including a second optical path portion and a second spacer portion surrounding the second optical path portion; and
   a sheet-shaped bonding portion including a curable resin film and bonding the first optical element and the second optical element, the sheet-shaped bonding portion including a center portion which is in contact with an optical path space, and a peripheral portion that bonds the first spacer portion and the second spacer portion and surrounds the center portion,
the manufacturing method comprising:
   a process of fabricating a first element wafer including the first optical element and a second element wafer including the second optical element;
   a process of preparing a bonding sheet including the curable resin film;
   a partial curing process of performing curing treatment on a predetermined region of the bonding sheet;
   a mirror-finishing process of processing a surface of the predetermined region into an optical flat surface;
   a process of fabricating a laminated wafer by laminating the first element wafer and the second element wafer, with the bonding sheet being disposed between the first element wafer and the second element wafer such that the predetermined region of the bonding sheet is opposed to the first optical path portion and the second optical path portion;
   a curing process of performing curing treatment on an uncured region of the bonding sheet in the laminated wafer; and
   a process of cutting the laminated wafer.

2. The manufacturing method of the optical unit for endoscope according to claim 1, wherein the partial curing process and the mirror-finishing process are simultaneously performed by a partial curing treatment on the bonding sheet, the bonding sheet being formed by a release substrate being crimped on a surface of the curable resin film, the release substrate having a release surface which is an optical flat surface.

3. The manufacturing method of the optical unit for endoscope according to claim 1, wherein the mirror-finishing process is a machining process of mechanically processing the surface of the predetermined region subjected to the curing treatment.

4. The manufacturing method of the optical unit for endoscope according to claim 3, further comprising, between the partial curing process and the machining process,
   a process of removing the curable resin film on the uncured region, and
   a process of disposing a second curable resin film on a region from which the curable resin film is removed.

5. The manufacturing method of the optical unit for endoscope according to claim 1, wherein the bonding sheet is a double-sided bonding sheet formed by disposing the curable resin film on both surfaces of a transparent parallel flat plate sheet.

\* \* \* \* \*